US00PP12645P2

(12) United States Plant Patent
Weatherly

(10) Patent No.: US PP12,645 P2
(45) Date of Patent: May 21, 2002

(54) FLORIBUNDA ROSE PLANT NAMED 'PROBRIL'

(75) Inventor: Lilia M. Weatherly, Austin's Ferry Tasmania (AU)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/488,386

(22) Filed: Jan. 20, 2000

(51) Int. Cl.[7] ..... A01H 5/00
(52) U.S. Cl. ..... Plt./141
(58) Field of Search ..... Plt./141

(56) References Cited

PUBLICATIONS

UPOV–ROM GTITM Computer Database 2001/01, Feb. 6, 2001, GTI Jouve Retrieval Software, Citation for 'PRObril'.*

* cited by examiner

*Primary Examiner*—Bruce R. Campell
*Assistant Examiner*—Annette H. Para
(74) *Attorney, Agent, or Firm*—Christie, Parker & Hale, LLP

(57) ABSTRACT

A new variety of Floribunda rose suitable for garden decoration, having flowers of deep pink and cream coloration.

1 Drawing Sheet

BACKGROUND OF THE INVENTION

This invention relates to a new and distinct variety of Floribunda Rose. The varietal denomination of the new variety is 'PRObril'. It was discovered in the Autumn of 1995 in Austins Ferry, Tasmania as a mutation of the cultivar 'PROberg' (U.S. Plant Pat. No. 9,600) in a controlled planting of the parent.

SUMMARY OF THE INVENTION

Among the features that distinguish the new variety from other presently available and known commercial rose cultivars are the following combination of characteristics: its cream colored flowers irregularly painted with deep pink, its prolific bloom and its dark pink stamens and anthers. The plant is a bushy upright growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagation. 'PRObril' may be asexually propagated by cuttings, budding or grafting.

COMPARISON WITH PARENTS

The new rose may be distinguished from its parent, 'PROberg', by the following combination of characteristics: whereas 'PROberg' bears flowers with light pink markings, 'PRObril' bears flowers with significantly darker pink colorations. 'PRObril' bears flowers with very dark pink stamens and anthers, whereas 'PROberg' bears flowers with significantly lighter pink stamens and anthers.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon The Colour Chart of The Royal Horticultural Society of London, England, except where common terms of color definition are employed.

DESCRIPTION OF THE NEW VARIETY

The following description is of 3 to 4 year-old rose plants of the new cultivar grown outdoors in Upland, Calif. in the month of October. Phenotypic expression may vary with environmental, cultural and climatic conditions, as well as differences in conditions of light and soil.

FLOWER

The new variety sometimes bears its flowers singly, usually in clusters of three to four or more per stem. Flowers are borne in irregular somewhat rounded clusters on slightly weak medium length stems (about 20 to about 30 cm.). Outdoors, the plant blooms very abundantly and nearly continuously during the growing season. The flowers have a slight fragrance.

BUD

The peduncle is about 4 to about 5 cm. in length, and usually erect to somewhat bending. It is moderately rough with numerous stipitate glands. Peduncle color is between 144A and 146B, sometimes lightly suffused with between 182A and 184C.

Before the calyx breaks, the bud is about 1 to about 1.4 cm. in diameter at the widest point, about 1.8 to about 2.2 cm. in length, and very pointed to somewhat ovoid in shape. The surface of the bud bears some stipitate glands usually with slender foliaceous parts entending beyond the tip of the bud about ¼ or more it its length. Bud color is between 144A and 146B.

The inner surface of the sepals is covered with very fine wooly tomentum; sepal margins are lined with some stipitate glands and numerous hairs; sepals are somewhat broadly lanceolate in shape, about 1.7 to about 2.1 cm in length and about 0.7 to about 0.9 cm in width at the widest point.

As the petals open (after the clayx breaks), the bud is about 1.2 to about 1.7 cm. in diameter at the widest point, about 1.9 to about 2.4 cm. in length, and very pointed to somewhat urn-shaped in form. The color of the under surfaces of the newly opened petals is between 155C and 155A sometimes blushed with between 64C and 64B. At the point where the petal attaches, there is a very small zone of near 4D. The color of the upper surfaces of the newly opened petals is irregularly marked with as dark as between 64B and 67A and as light as between 67C and 68B. At the point where the petal attaches, there is a moderately large zone of between 155A and 4D.

BLOOM

When fully open, the bloom ranges from about 7 to about 9 cm. in diameter. Petalage is double with about 27 to 32 petals and about 1 to 3 petaloids arranged irregularly. When partially open, the bloom form is moderately high centered and the petals are somewhat loosely spiraled to cupped with petal edges slightly reflexed outward. When fully open, the bloom form is more flat to somewhat cupped, and the petals are somewhat cupped to undulated with petal edges only slightly rolled outward.

PETALS

The substance of the petals is somewhat thin with upper surfaces moderately satiny and under surfaces slightly shiny. The outer petals are nearly round to broadly obovate in shape mostly with rounded apices. Petals are about 2.2 to about 3.6 cm in length and about 2.8 to about 3.4 cm in width at the widest point. The inner petals are more narrowly obovate in shape with rounded apices.

NEWLY OPENED FLOWER

The under surface of the outer, intermediate and inner petals is between 155A and 155C. There is no variation in color at the point of attachment.

The upper surface of the outer, intermediate and inner petals is irregularly marked with as dark as between 64B and 67A and as light as between 68D and 73C. At the point where the petal attaches, there is a moderately large zone of near 155A.

The general tonality of the newly opened flower is irregularly marked with as dark as between 64B and 67A and as light as between 68D and 73C with a reverse of between 155A and 155C.

THREE DAY OLD FLOWER

The under surface of the outer and inner petals is between 155B and 155D. There is no variation in color at the point of attachment.

The upper surface of the outer and inner petals is irregularly marked with as dark as between 68A and 67B and as light as between 69A and 73D. At the point where the petal attaches, there is a moderately large zone of near 155B.

The general tonality of the three day old flower is irregularly marked with as dark as between 68A and 67B and as light as between 69A and 73D with a reverse of between 155B and 155D.

The petals usually drop away cleanly on the spent blooms.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average to many in number (approximately 85) and are arranged regularly about the pistils. Pistils are usually about 0.2 to 0.3 cm in length. The filaments are of medium to long length, most with anthers. Filaments are between 59B and 60C in color. The anthers are moderately small, usually less than 0.1 cm in length, for the class and all open approximately at the same time. Anther color is between 59B and 60C when immature and near 200B at maturity. Pollen is abundant and near 14D in color.

FEMALE REPRODUCTIVE ORGANS

Pistils vary in number (approximately 35). The styles are somewhat uneven, short to average in length, average in caliper, and moderately bunched. Stigma color is near 4D. Style color is near 45C. Ovaries are usually all enclosed in the calyx.

Hips are of moderately long, somewhat pointed to ovoid in form, and near 34D in color when ripe. The hip surface is very smooth with thick fleshy walls. The sepals are fugacious. There are approximately 6 to 14 large seed.

FOLIAGE

The compound leaves are usually comprised of three to five or more leaflets and are borne abundantly. The leaves are about 7.5 to about 11.5 cm. in length and about 6 to about 9.5 cm. in width at the widest point, moderately heavy in texture, and semi-glossy in finish. The terminal leaflets are about 4.5 to about 6 cm. in length and about 2.5 to about 3.4 cm. in width at the widest point, mostly ovoid to somewhat oblong in shape with acute apices and acute to somewhat round bases. Their margins are simply serrate.

The upper surface of the mature leaf is between 147A and 137B. The under surface of the mature leaf is between 139A and 147C. The upper surface of the young leaf is between 144A and 137D, sometimes lightly suffused with near 183C. The under surface of the young leaf is near 138B, sometimes lightly suffused with near 183D.

The rachis is somewhat light to average in caliper and moderately smooth. The upper side is shallowly grooved with some stipitate glands on the edges of the grooves. The under side of the rachis is moderately smooth with few stipitate glands. The rachis of the young leaves are usually moderately suffused with near 183C.

The stipules are about 5 to about 7 cm. in length and moderately narrow width with moderately long straight points that usually turn out at an angle of less than 45 degrees. The stipules of the young leaves are usually moderately suffused with near 183C.

The plant displays an above average degree of resistance to powdery mildew, blackspot and rust as compared to other commercial varieties grown under comparable conditions in Upland, Calif.

GROWTH

The plant has a bushy upright medium height growth habit (about 75 to about 90 cm. in height and about 80 to about 100 cm. spread at the widest point), with very full branching. It displays very vigorous growth and the canes are of somewhat light caliper.

The color of the major stems is between 144B and 148A. They bear very few medium sized and small prickles that are about 0.3 to about 0.6 cm. in length. The prickles are almost straigt angled slightly downward with a somewhat short to medium moderately broad to nearly round base; prickle color is between 164A and 166B.

The color of the branches is between 144A and 146B. They bear very few medium sized and small prickles which are of similar size and shape to the prickles on the major stems; prickle color is between 160B and 162C.

The color of the new shoots is near 144A often moderately suffused with between 183D and 181C. They bear very few medium sized and small prickles which are of similar size and shape to the large prickles on the major stems; prickle color is near 162D often moderately suffused with between 183D and 181C.

I claim:

1. A new and distinct Floribunda rose plant of the variety substantially as described and illustrated herein.

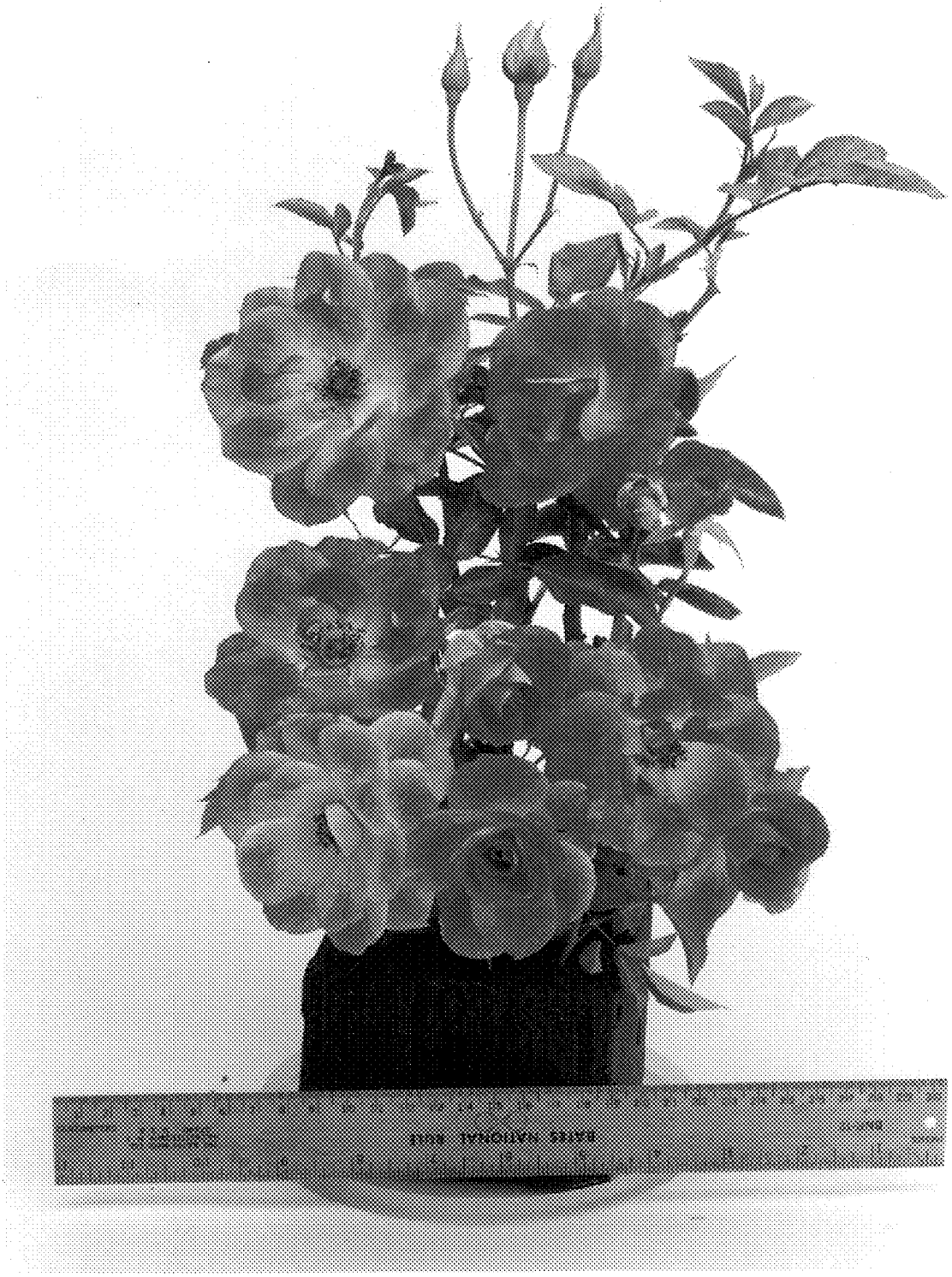

* * * * *